(12) United States Patent
Miyajima et al.

(10) Patent No.: US 11,042,967 B2
(45) Date of Patent: Jun. 22, 2021

(54) IMAGE PROCESSING METHOD

(71) Applicant: Shimadzu Corporation, Kyoto (JP)

(72) Inventors: Takahiro Miyajima, Kyoto (JP); Junya Yamamoto, Kyoto (JP); Kazuyoshi Nishino, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 79 days.

(21) Appl. No.: 16/488,965

(22) PCT Filed: Feb. 26, 2018

(86) PCT No.: PCT/JP2018/006971
§ 371 (c)(1),
(2) Date: Aug. 27, 2019

(87) PCT Pub. No.: WO2018/159535
PCT Pub. Date: Sep. 7, 2018

(65) Prior Publication Data
US 2020/0013147 A1 Jan. 9, 2020

(30) Foreign Application Priority Data
Feb. 28, 2017 (JP) .............................. JP2017-036767

(51) Int. Cl.
G06T 3/60 (2006.01)
G06T 7/30 (2017.01)
G06T 7/70 (2017.01)

(52) U.S. Cl.
CPC ................ G06T 3/60 (2013.01); G06T 7/30 (2017.01); G06T 7/70 (2017.01); G06T 2207/10081 (2013.01)

(58) Field of Classification Search
None
See application file for complete search history.

(56) References Cited

U.S. PATENT DOCUMENTS

2005/0129180 A1* 6/2005 Tsujii .................... A61B 6/488
378/195
2012/0265050 A1* 10/2012 Wang ................... A61B 5/0035
600/411

FOREIGN PATENT DOCUMENTS

JP 2007-300966 A 11/2007

OTHER PUBLICATIONS

International Search Report for PCT application PCT/JP2018/006971, dated Apr. 10, 2018.
(Continued)

Primary Examiner — Leon Flores
(74) Attorney, Agent, or Firm — Muir Patent Law, PLLC

(57) ABSTRACT

A center of gravity of a chest front image is obtained by a center of gravity calculation using pixel values in the chest front image, and a vicinity pixel position of the center of gravity is set as a center position P of a circular search region having a radius of a predetermined length. The shortest line segment of four line segments obtained by drawing perpendicular lines down from the center position P of an irradiation field to boundary lines of the upper, lower, left and right irradiation fields. The line segment, which is a radius of the circular search region, is rotationally displaced for each predetermined angle θ, and the profile of the average value for each predetermined angle θ is obtained. From the displacement angle θ of the line segment in which the average value becomes minimum, the orientation of the subject from the head to the abdomen reflected in the chest front image is determined. On the other hand, the displacement angle θ of the two line segments (diameter line segment) in which the sum of the average values of the two line segments (diameter line segments) opposed at 180° in the profile of the average value is obtained as an inclination angle of the chest front image.

7 Claims, 12 Drawing Sheets

(56) References Cited

OTHER PUBLICATIONS

Written Opinion of the International Search Authority for PCT application PCT/JP2018/006971, dated Apr. 10, 2018.

* cited by examiner (a)

(b)

IMAGE PROCESSING METHOD

TECHNICAL FIELD

The present invention relates to an image processing method of a chest front image obtained by performing X-ray imaging of a chest of a subject from the front.

BACKGROUND ART

In a chest front image obtained by performing X-ray imaging of a chest of a subject from the front, in addition to lung fields of the subject, the centrum and internal organs of the subject are reflected. In a centrum and internal organs of a subject, X-rays are absorbed, so their pixel values are low. On the other hand, outside the subject, X-rays are directly incident on an X-ray detector, so their pixel values are high. In lung fields of a subject, X-rays are absorbed more than the outside of the subject and transmitted therethrough more than the centrum and internal organs of the subject. Therefore, in lung fields of a subject, the pixel values are lower than those of the outside of the subject and the pixel values are higher than those in the centrum or internal organs of the subject.

Pixel values in lung fields are similar to each other. Therefore, when a contrast adjustment is performed on the entire chest front image for the purpose of increasing the visibility of the lung fields, the contrast adjustments are made including the centrum and internal organs of the subject and even outside the subject. As a result, the high luminance values on the monitor are used to represent the outside of the subject, and low luminance values on the monitor are used to represent centrum and internal organs. In the lung fields, the visibility is not improved so much. Therefore, there is a technique for improving the visibility of lung fields by extracting the lung field regions and contrast adjusting only the extracted lung field regions (see, for example, Patent Document 1).

PRIOR ART

Patent Document

Patent Document 1: Japanese Unexamined Patent Application Publication No. 2007-300966

SUMMARY OF THE INVENTION

Problems to be Solved by the Invention

However, in the case of such a conventional contrast adjustment, there is a problem that an orientation of a subject from a head to an abdomen reflected in a chest front image has not been considered.

The present invention has been made in view of the aforementioned circumstances, and aims to provide an image processing method capable of accurately detecting an orientation of a subject reflected in a chest front image.

Means for Solving the Problems

In order to attain such an object, the present invention has the following configuration.

That is, the image processing method according to the present invention is an image processing method of a chest front image. The method includes:

a center of gravity calculation step of obtaining a center of gravity of a chest front image by a center of gravity calculation using pixel values in the chest front image;

a search region setting step of setting the center of gravity or its vicinity pixel position as a center of a circular search region having a radius of a predetermined length;

an evaluation value profile calculation step of obtaining a profile of an evaluation value for each predetermined angle by setting an average value or an addition value of pixel values on a line segment which is a radius of the circular search region as the evaluation value and rotationally displacing the line segment for each predetermined angle;

an orientation determination step of determining an orientation of a subject from a head to an abdomen reflected in the chest front image from a displacement angle of the line segment in which the evaluation value becomes a minimum value in the profile of the evaluation value; and an inclination angle calculation step of obtaining a displacement angle of the two line segments in which a sum of the evaluation values on two line segments opposed at 180° in the profile of the evaluation value as an inclination angle of the chest front image.

[Functions and Effects] According to the image processing method of the present invention, in the center of gravity calculation step, the center of gravity of the chest front image is obtained by the center of gravity calculation using pixel values in the chest front image. As described above, pixel values in a centrum of a subject are low. Therefore, the center of gravity of the chest front image obtained by the center of gravity calculation using the pixel values in the chest front image or its vicinity pixel position is estimated to be positioned on the centrum. In the search region setting step, the center of gravity or its vicinity pixel position is set as a center of a circular search region having a radius of a predetermined length. In the evaluation value profile calculation step, the average value or addition value of the pixel values on the line segment which is a radius of the circular search region is set as an evaluation value, and the line segment is rotatably displaced every predetermined angle, and the profile of the evaluation value for each predetermined angle is obtained.

In the chest front image, bronchus are reflected at the upper portion of the image and a lower abdomen such as internal organs is reflected at the lower portion of the image, so in general, their pixel values become small at the lower portion of the centrum. Therefore, in the orientation determination step, it is estimated that the line segment in which the evaluation value in the profile of the evaluation value becomes a minimum value correspond to the lower portion of the centrum, and the orientation of the subject from the head to the abdomen reflected in the chest front image can be determined from the displacement angle of the line segment in which the evaluation value becomes a minimum value.

On the other hand, in the inclination angle calculation step, the displacement angle of two line segments (diameter line segment) in which the sum of evaluation values of two line segments (i.e., diameter line segment) opposed at 180° in the profile of the evaluation values becomes a minimum value is obtained as the inclination angle of the chest front image. It is estimated that two line segments (diameter line segment) in which the sum of evaluation values becomes a minimum value correspond to the entire centrum including the upper portion of the centrum, so that the inclination angle of the chest front image can be obtained with higher accuracy. As a result, the orientation of the subject reflected in the chest front image can be detected with high accuracy.

In the image processing method according to the present invention, the above-described vicinity pixel position (of the center of gravity) is a coordinate of a pixel in which the pixel value becomes minimum in a rectangular region centered on the center of gravity. In cases where the center of gravity of the chest front image calculated by the center of gravity calculation using pixel values in the chest front image is not positioned on the centrum, the coordinate of the pixel is finely adjusted so that the vicinity pixel position is positioned on the centrum by searching the coordinate of the pixel in which the pixel value becomes minimum in the rectangular region centered on the center of gravity and setting the coordinate as the center of the circular search region. The range of the rectangular region may be set as appropriate according to the resolution of the image, the compression ratio of the image, and the like.

In cases where a subject is a child, the centrum may deviate significantly from the center of the image. In this case, a significant misalignment occurs between the center of gravity of the chest front image obtained by the center of gravity calculation using pixel values in the chest front image and the centrum. Therefore, even if the above-mentioned method is adopted in which the coordinate of the pixel in which the pixel value becomes minimum in the rectangular region centered on the center of gravity is set as the vicinity pixel position of the center of gravity, the rectangular region which becomes a search range becomes very large, so that the amount of calculation increases. Alternatively, even if the rectangular region which becomes a search range is expanded, the pixel in which the pixel value becomes minimum in the rectangular region is not always positioned on the centrum. Therefore, in the image processing method according to the present invention, the method preferably further includes a pixel value inversion step of inverting pixel values in the chest front image, wherein in the center of gravity calculation step, the center of gravity is obtained by the center of gravity calculation using inverted pixel values.

The reason why the pixel values are inverted will be described with reference to FIG. 8. In FIG. 8, it is assumed that the centrum in which the pixel value is low (the pixel value is 0 in (a) of FIG. 8) is positioned at the lower left pixel of the image of vertical and horizontal 3×3 pixels, the maximum pixel value is 10, and the pixel values in pixels other than the centrum are uniformly 10. When the pixel values are not inverted as shown in (a) of FIG. 8, the center of gravity G is biased from the center of the image to the upper right as shown in (b) of FIG. 8. That is, as a result that it has become the state in which the lower left pixel whose pixel value is 0 is substantially missing, the position deviated from the center of the image in the upper right direction becomes the center of gravity G.

On the other hand, by inverting pixel values, the pixel value in the lower left pixel where the centrum is positioned is inverted to 10 and pixel values of the pixels other than the centrum are inverted to 0 as shown in (c) of FIG. 8. When inverted as shown in (c) of FIG. 8, the center of gravity G is positioned at the center of the lower left pixel where the centrum is positioned by the center of gravity calculation using the inverted pixel value at the lower left pixel where the centrum is positioned as shown in (d) of FIG. 8. In other words, it becomes the state in which the pixels other than the centrum whose the inverted pixel value became 0 due to the inversion of the pixel value are substantially missing, so the center of the lower left pixel where the centrum is positioned becomes the center of gravity G.

In this way, even if the centrum deviates significantly from the center of the image, by obtaining the center of gravity by the center of gravity calculation using inverted pixel values, the center of gravity can be accurately obtained as a pixel positioned on the centrum. Note that the above-mentioned method in which the coordinate of the pixel in which the pixel value becomes minimum in the rectangular region centered on the center of gravity is set as the vicinity pixel position of the center of gravity and the above-mentioned method in which the center of gravity is obtained by the center of gravity calculation using inverted pixel values may be combined.

In this case, a pixel value inversion step of inverting pixel values in the chest front image is provided, and in the center of gravity calculation step, the center of gravity is obtained by the center of gravity calculation using the inverted pixel values, and the vicinity pixel position (of the center of gravity) is a coordinate of a pixel in which the pixel value becomes minimum in the rectangular region centered on the center of gravity in the chest front image in which the pixel value is not inversed. In other words, in the case of obtaining the center of gravity, the inverted pixel values are used. In the case of setting the coordinate of the pixel in which the pixel value becomes minimum in the rectangular region centered on the center of gravity as a vicinity pixel position of the center of gravity, the chest front image in which the pixel values are not inverted is used.

Here, it should be noted that the pixel value inversion step of inverting the pixel values in the chest front image is not essential in the present invention. What is desired to finally obtain in the present invention is the orientation of the subject or the inclination angle, not the position of the center of gravity. Therefore, if pixel values are not inversed when the centrum deviates significantly from the center of the image, a large background region outside the subject is included in the circular search region in which the line segment is a radius. On the other hand, if the pixel values are inverted when the centrum deviates significantly from the center of the image, the background region outside the subject is not included in the circular search region in which the line segment is a radius, which means that when pixel values are inverted, the orientation of the subject and the inclination angle thereof can be obtained more accurately as compared with the case in which pixel values are not inverted. In other words, even if the pixel value inversion step of inverting the pixel values in the chest front image is not provided, the background region outside the subject is merely included in the circular search region in which the line segment is a radius, which means that the orientation of the subject and the inclination angle thereof can be determined with a certain degree of accuracy.

As described above, the pixel values are small in the lower abdomen as well as the centrum. Therefore, when the above-described method for obtaining the center of gravity by the center of gravity calculation using inverted pixel values is adopted, there is a possibility that the center of gravity or its vicinity pixel position is positioned in the lower abdomen of the centrum where there is no lung fields. Therefore, in the image processing method according to the present invention, the method further includes a pixel value setting step of preforming setting of replacing a pixel value in the chest front image with a preset threshold value when the pixel value is lower than the preset threshold value, and performing setting the pixel value in the chest front image as a value of the pixel value itself without replacing the pixel value when the pixel value is equal to or higher than the threshold value, wherein in the pixel value inversion step, the pixel value set in the pixel value setting step is inverted, and wherein in the center of gravity calculation step, the center of gravity of the chest front image is obtained by the center of gravity calculation using the inverted pixel values The reason why the pixel values are replaced with the threshold value when the pixel values in the chest front image are lower than the threshold value will be described with reference to FIG. 9. In FIG. 9, for the sake of convenience, the image before the pixel value inversion is shown. As described above, the lower abdomen includes internal organs. In general, the pixel values in the lower abdomen are lower than the pixel values in the centrum. In cases where the above-mentioned method of obtaining the center of gravity by the center of gravity calculation using pixel values after the inversion is adopted, when the pixel values in the lower abdomen are inversed as they are and used for the center of gravity calculation, the center of gravity and its vicinity pixel position are detected as being positioned at the lower abdomen of the centrum where there are no lung fields. That is, as shown in (a) of FIG. 9, the center position P of the circular search region which is the center of gravity or its vicinity pixel position is detected as being positioned at the lower abdomen of the centrum where there are no lung fields. Therefore, as a result that no lung fields exist on the left and right sides of the center of gravity, when obtaining a line segment in which the evaluation value or the sum of evaluation values becomes a minimum value in the profile of the evaluation value, the average value or the addition value will be calculated using the pixel values in the lower abdomen lower than the pixel values in the centrum. That is, when the center position P is detected as being positioned at the lower abdomen of the centrum, an evaluation value (average value or addition value) on the line segment L shown in (b) of FIG. 9 passing through the lower abdomen in a direction not parallel to the centrum direction (for example, a direction perpendicular to the centrum) is obtained as a minimum value. As a result, by inverting the pixel values in the lower abdomen lower than the pixel values in the centrum as they are and using them for the center of gravity calculation, there is a possibility that the orientation of the subject cannot be detected with high accuracy.

Therefore, the pixel value in the centrum is preset as a threshold value. In the pixel value setting step, the pixel value in the lower abdomen is set by replacing it with the threshold value (so-called "round to a threshold value"), and the pixel value set in the pixel value setting step is inverted and used for the center of gravity calculation. Thus, the center of gravity and its vicinity pixel position are detected as being positioned at the upper portion of the centrum where lung fields exist.

As described above, even if the pixel values in the lower abdomen are lower than the pixel values in the centrum, the pixel values in the lower abdomen are set by replacing them with the threshold value and the set pixel values are inverted and used for the center of gravity calculation so that the center of gravity and its vicinity pixel position can be detected as being positioned at the upper portion of the centrum where lung fields exist. And by obtaining the average value or the addition value using the pixel values in the lower abdomen set by being replaced with the threshold value, the evaluation value (average value or addition value) on a line segment parallel to the centrum direction and passing through the centrum can be obtained as a minimum value. As a result, the orientation of the subject can be detected with high accuracy. The above description is directed to the case in which the pixel values are rounded to the threshold value when the above-described method of calculating the center of gravity by the center of gravity calculation using pixel values after inversion is adopted. However, the above-described method in which the coordinate of the pixel in which a pixel value becomes minimum in the rectangular region centered on the center of gravity is set as the vicinity pixel position of the center of gravity may be further combined.

In the above-described search region setting step, a shortest line segment of the four line segments obtained by drawing perpendicular lines down from the center of gravity or its vicinity pixel position to boundary lines of the irradiation field is set as a radius of a circular search region. By setting the shortest line segment of the four line segments obtained by drawing perpendicular lines down from the center of gravity or its vicinity pixel position to the boundary lines of the irradiation field as a radius of a circular search region, pixels outside the irradiation field are prevented from being included in the circular search region.

Of course, in the above-described search region setting step, the shortest line segment of the four line segments obtained by drawing perpendicular lines down from the center of gravity or its vicinity pixel position to the boundary lines of the irradiation field may not be set as a radius of the circular search region. For example, in the search region setting step, a line segment having a predetermined length shorter than the shortest line segment of the four line segments obtained by drawing perpendicular lines down from the center of gravity or its vicinity pixel position to the boundary lines of the irradiation field may be set as a radius of the circular search region. However, in the above-described search region setting step, like the former method, according to the method in which the shortest line segment of the four line segments obtained by drawing perpendicular lines down from the center of gravity or its vicinity pixel position to the boundary lines of the irradiation field is set as a radius of a circular search region, more information of pixels included in the circular search region can be obtained. Therefore, in the former method, the orientation of the subject can be determined with higher accuracy, and the inclination angle of the chest front image can be determined with higher accuracy.

In an example of the image processing method according to the present invention, in the orientation determination step, the orientation of the subject is determined from the inclination angle obtained in the inclination angle calculation step. The order of the above-described orientation determination step and the above-described inclination angle calculation step is not particularly limited. However, in cases where there is a plurality of displacement angles at which the evaluation value becomes a minimum value only with a displacement angle at which a evaluation value on the line segment which is a radius of the circular search region becomes a minimum value, there is a risk that the orientation of the subject cannot be determined accurately. Furthermore, there may be a case in which a line segment in which the evaluation value becomes a minimum value does not necessarily correspond to the lower portion of the centrum due to the pixel values in the lower abdomen lower than the pixel values in the centrum as described above.

Therefore, in the above-mentioned inclination angle calculation step, the displacement angle of two line segments (diameter line segment) in which the sum of evaluation values becomes a minimum value on two line segments (diameter line segment) opposed at 180° in the profile of the evaluation value is obtained as the inclination angle of the chest front image. With this, it is possible to narrow down the inclination angle of two line segments (diameter line segment) in which the sum of evaluation values becomes a minimum value from candidates for the displacement angle in which the evaluation value on a plurality of narrowed-down line segments as an inclination angle of the chest front image. Further, even if the line segment in which the evaluation value becomes a minimum value does not necessarily correspond to the lower portion of the centrum due to the pixel values in the lower abdomen lower than the pixel values in the centrum, it is possible to obtain the displacement angle of the two line segments (diameter line segment) as the inclination angle of the chest front image in consideration of the evaluation value of the line segments opposed at 180° corresponding to the upper portion of the centrum. Then, in the orientation determination step described above, when the orientation of the subject is determined from the obtained inclination angle, the orientation of the subject can be accurately determined. Therefore, by determining the orientation of the subject in the orientation determination step after the inclination angle has been strictly determined in the inclination angle calculation step, the orientation of the subject can be accurately determined.

Effects of the Invention

According to the image processing method of the present invention, in the center of gravity calculation step, it is estimated that the center of gravity or its vicinity pixel position is positioned on the centrum by obtaining the center of gravity of the chest front image by the center of gravity calculation using pixel values in the chest front image. In the search region setting step, the center of gravity or its vicinity pixel position is set as the center of the circular search region having a radius of a predetermined length. In the evaluation value profile calculation step, the profile of the evaluation value for each predetermined angle is obtained by setting the average value or the addition value of the pixel value on the line segment which is a radius of the circular search region as the evaluation value and rotatably displacing the line segment every predetermined angle.

In the orientation determination step, it is estimated that the line segment in which the evaluation value becomes a minimum value in the profile of the evaluation value corresponds to the lower portion of the centrum, and the orientation of the subject from the head to the abdomen reflected in the chest front image can be determined from the displacement angle of the line segment in which the evaluation value becomes a minimum value.

On the other hand, in the inclination angle calculation step, the displacement angle of two line segments (diameter line segment) in which the sum of evaluation values on two line segments (diameter line segment) opposed at 180° in the profile of the evaluation value becomes a minimum value is obtained as the inclination angle of the chest front image. The two line segments (diameter line segment) in which the sum of evaluation values becomes a minimum value are estimated to correspond to the entire centrum including the upper portion of the centrum, so the inclination angle of the chest front image can be obtained with higher accuracy. As a result, the orientation of the subject reflected in the chest front image can be detected with high accuracy.

EXAMPLES

Reference Example

First, a reference example for introducing an example of the present invention will be described.

Figure 10:
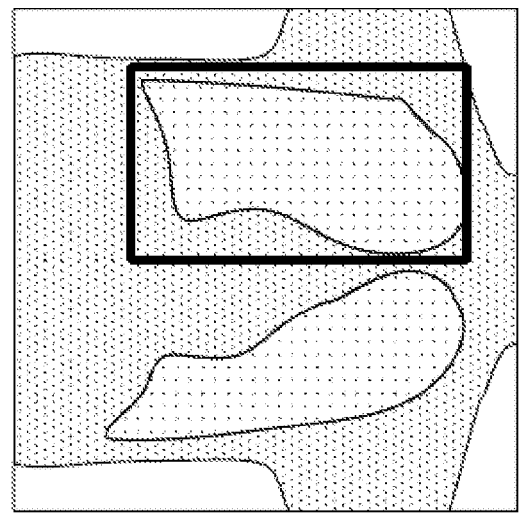
FIG. 10 is a schematic diagram of a problem when a lung field region is extracted in cases where the subject reflected in the chest front image is shown horizontally.

For example, as shown in FIG. 10, in cases where the head of the subject is positioned on the right side and the subject whose chest front image is reflected sideways, when trying to extract the lung field region, there occurs a possibility that only the right lung image (see the thick frame in FIG. 10) is misidentified as a lung field. In cases where the head is positioned on the right side and the subject is reflected sideways, although there exists a left lung image under the right lung image, only the right lung image is misidentified as a lung field. As a result, a contrast adjustment is performed only for the right lung image, so a contrast adjustment cannot be performed correctly.

Figure 11:
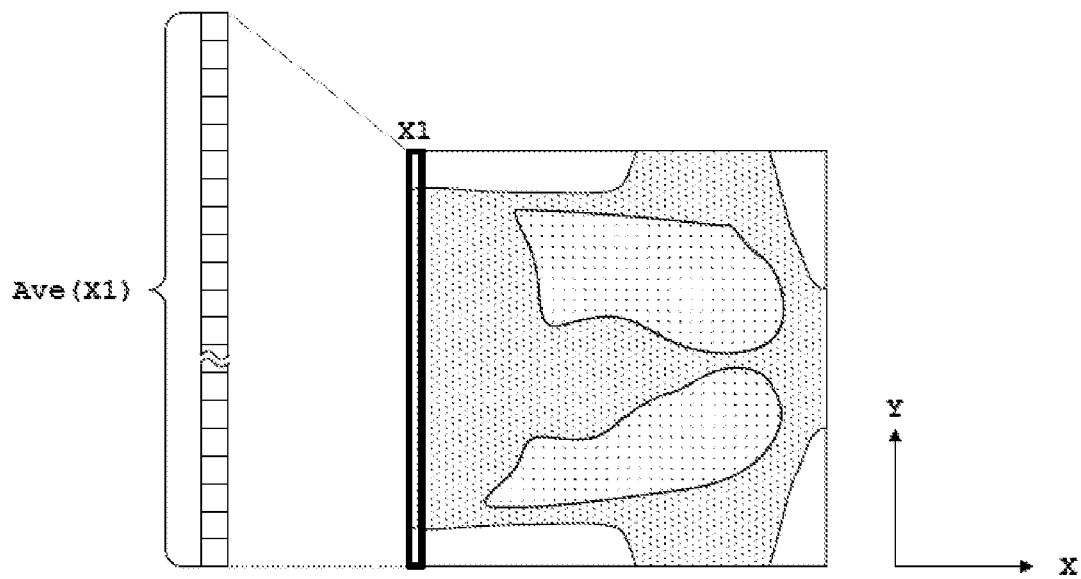
FIG. 11 is a schematic diagram of a profile according to a reference example in which the coordinate (X-coordinate) of the pixel row of the image is shown on the horizontal axis and the average value or addition value of the pixel value in the pixel column (Y-direction) of the image is shown on the vertical axis.
Figure 12:
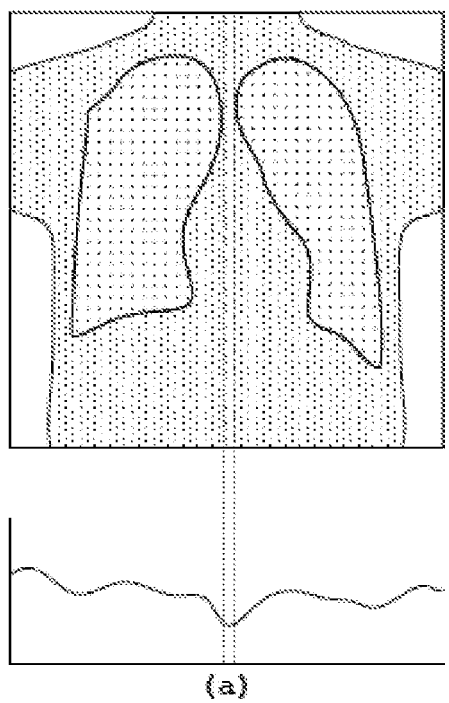
FIG. 12 shows schematic diagrams of the profile, wherein (a) is a schematic diagram of a profile when a head is positioned on the upper or lower side (the subject is reflected vertically) and (b) is a schematic diagram of a profile when a head is positioned on the left or right side (the subject is reflected horizontally).
Figure 12:
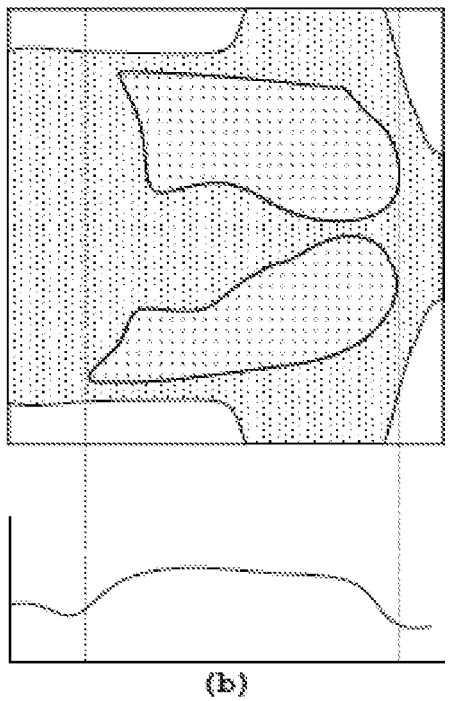

Therefore, as shown in FIG. 11 to FIG. 14, it is conceivable to consider the orientation of the subject. First, as shown in FIG. 12, it is determined whether the subject is reflected vertically or horizontally. Therefore, a profile is generated in which the coordinate (X-coordinate) of the pixel row of the image is shown on the horizontal axis and the average value or addition value of the pixel value in the pixel column (Y-direction) of the image is shown on the vertical axis as shown in FIG. 11. In cases where the head is positioned on the upper side or lower side (the subject is reflected vertically) as shown in (a) of FIG. 12, the average value or the addition value becomes a minimum value in the center portion of the image corresponding to the portion between the left lung field and the right lung field. On the other hand, in cases where the head is positioned on the left or right side (the subject is reflected horizontally) as shown in (b) of FIG. 12, the average value or the addition value becomes a minimum value at the end portions of the image where there exist no lung fields.

Figure 13:
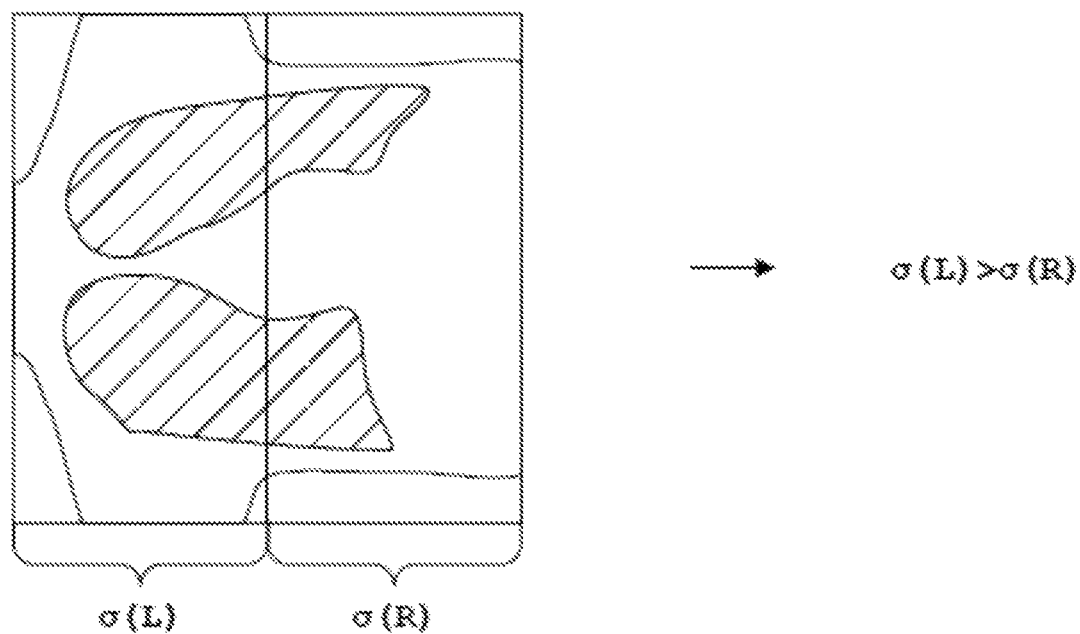
FIG. 13 is a schematic diagram used for explaining right-left determination processing according to a reference example.
Figure 14:
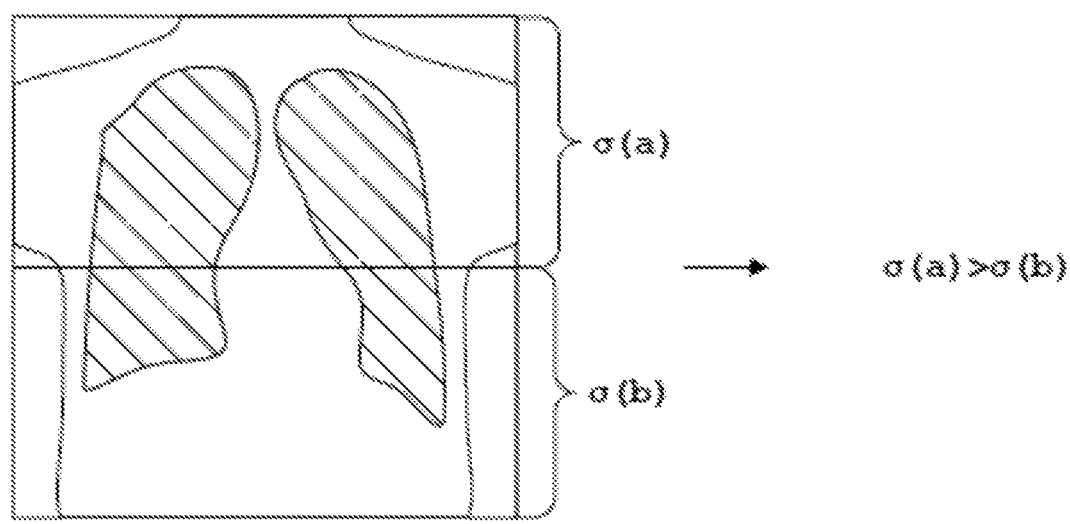
FIG. 14 is a schematic diagram used for explaining up-down determination processing according to a reference example.

Next, it is specified that the head is positioned at which position of the upper, lower, right and left positions. For this purpose, an edge extraction image of the input image is generated. In cases where it is determined that the subject is reflected horizontally, the standard deviation σ(L) of the pixel value in the left half of the edge extraction image and the standard deviation σ(R) of the pixel value in the right half thereof are calculated as shown in FIG. 13. In cases where it is determined that the subject is reflected vertically, the standard deviation σ(a) of the pixel value in the upper half of the edge extraction image and the standard deviation σ(b) of the pixel value in the lower half thereof are calculated as shown in FIG. 14. On the side where lungs are reflected, the standard deviation becomes higher due to the edges of ribs, and therefore it is determined that there is a head on the side where the higher standard deviation is higher. In FIG. 13, the standard deviation σ(L) of the pixel value in the left half is higher than the standard deviation σ(R) of the pixel value in the right half (σ(L)>σ(R)), and therefore it is determined that there is a head on the left side of the higher standard deviation. In FIG. 14, the standard deviation σ(a) of the pixel value in the upper half is higher than the standard deviation σ(b) of the pixel value in the lower half (σ(a)>σ(b)), and therefore it is determined that there is a head on the upper side of the higher standard deviation.

In this way, it is possible to accurately extract the lung fields regardless of whether the head is positioned on the upper, lower, left, or right side. As a result, regardless of whether the head is positioned on the upper, lower, left, or right side, the contrast adjustment of only the lung fields can be performed correctly, so that the visibility of the lung fields can be improved.

However, in cases where the image is inclined, there is a problem that the detection accuracy of the lung fields decreases. In particular, in the case of performing X-ray imaging using a mobile vehicle, the X-ray imaging is performed by moving the mobile vehicle to a bed on which a subject is placed. In this case, the X-ray irradiation field tends to be inclined with respect to the X-ray detector. As a result, the obtained image is also inclined. When generating the profile described above, pixels are scanned in the vertical direction of the pixel column (X-direction in the case of FIG. 11 to FIG. 14) regardless of the orientation of the subject. For this reason, the pixel value of the pixel in a region deviated from the chest, such as an arm and an air region (for example, a region outside the subject), is added and used for the direction determination. Therefore, an example of the present invention is introduced in consideration of the case where it is inclined in the oblique direction as described below.

EXAMPLES

Hereinafter, examples of the present invention will be described with reference to the drawings.

Figure 1:
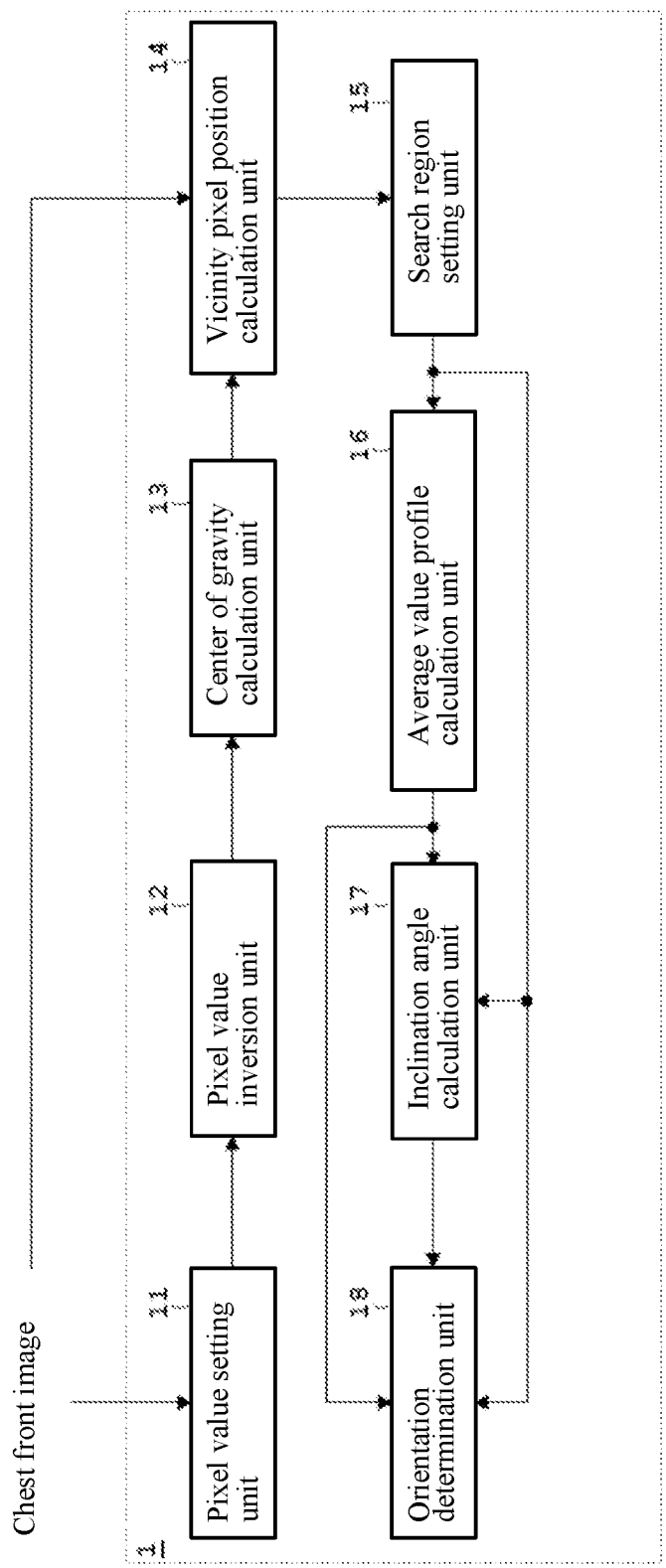
FIG. 1 is a block diagram of an image processing apparatus according to an example.

FIG. 1 is a block diagram of an image processing apparatus according to an example. In this example, the description will be made by exemplifying an image obtained by X-ray imaging by a mobile vehicle (mobile X-ray imaging apparatus) as a chest front image. In this example, the description will be made by exemplifying an average value (also called "addition average value" or "arithmetic average value") as an evaluation value.

As shown in FIG. 1, the image processing apparatus 1 according to this example is provided with a pixel value setting unit 11, a pixel value inversion unit 12, a center of gravity calculation unit 13, a vicinity pixel position calculation unit 14, a search region setting unit 15, and an average value profile calculation unit 16, an inclination angle calculation unit 17, and an orientation determination unit 18. The image processing apparatus 1 is composed of, e.g., a GPU (Graphics Processing Unit), a central processing unit (CPU), or a programmable device (for example, an FPGA (Field Programmable Gate Array) capable of changing a hardware circuit (for example, a logic circuit) used inside in accordance with program data.

The pixel value setting unit 11 sets, when pixel values in the chest front image are smaller than a preset threshold value, the pixel values by replacing the pixel values with a threshold value, and sets, when the pixel values in the chest front image is equal to or higher than the threshold value, the pixel values as the values themselves without replacing the pixel values with the threshold value. The specific functions of the pixel value setting unit 11 will be described later with reference to FIG. 2. The pixel values set in the pixel value setting unit 11 are sent to the pixel value inversion unit 12.

The pixel value inversion unit 12 inverts the pixel values in the chest front image set in the pixel value setting unit 11. The specific functions of the pixel value inversion unit 12 will be described later with reference to FIG. 2. The pixel values inverted by the pixel value inversion unit 12 are sent to the center of gravity calculation unit 13.

The center of gravity calculation unit 13 obtains the center of gravity of the chest front image by the center of gravity calculation using pixel values inverted by the pixel value inversion unit 12 in the chest front image. The specific functions of the center of gravity calculation unit 13 will be described later with reference to FIG. 2. The center of gravity obtained by the center of gravity calculation unit 13 is sent to the vicinity pixel position calculation unit 14.

The vicinity pixel position calculation unit 14 obtains the coordinate of a pixel in which the pixel value becomes minimum in a rectangular region centered on the center of gravity obtained by the center of gravity calculation unit 13 in the chest front image in which the pixel values are not inverted, as the vicinity pixel position of the center of gravity. The specific functions of the vicinity pixel position calculation unit 14 will be described later with reference to FIG. 2 and FIG. 3. The vicinity pixel position of the center of gravity calculated in the vicinity pixel position calculation unit 14 is sent to the search region setting unit 15.

The search region setting unit 15 sets the vicinity pixel position of the center of gravity obtained by the vicinity pixel position calculation unit 14 in the chest front image as the center of the circular search region having a radius of a predetermined length. The specific functions of the search region setting unit 15 will be described later with reference to FIG. 2 and FIG. 4. The circular search region determined by the search region setting unit 15 is sent to the average value profile calculation unit 16, the inclination angle calculation unit 17, and the orientation determination unit 18.

The average value profile calculation unit 16 obtains the average value of the pixel values on the line segment which is a radius of a circular search region. Then, the line segment is rotationally displaced for each predetermined angle to obtain an average value for each predetermined angle. In this way, a profile of the average value is generated with the predetermined angle shown on the horizontal axis and the average value shown on the vertical axis. The specific functions of the average value profile calculation unit 16 will be described later with reference to FIG. 2, FIG. 4, and FIG. 5. The profile of the average value for each predetermined angle obtained by the average value profile calculation unit 16 is sent to the inclination angle calculation unit 17 and the orientation determination unit 18.

The inclination angle calculation unit 17 obtains the inclination angle of two line segments (diameter line segment) in which the sum of the average values of two line segments (i.e., diameter line segment) opposed at 180° in the profile of the average value obtained in the average value profile calculation unit 16 becomes a minimum value as the displacement angle of the chest front image. The specific functions of the inclination angle calculation unit 17 will be described later with reference to FIG. 2, FIG. 6, and FIG. 7. The inclination angle calculated by the inclination angle calculation unit 17 is sent to the orientation determination unit 18.

The orientation determination unit 18 determines the orientation of the subject reflected in the chest front image from the inclination angle obtained by the inclination angle calculation unit 17. The specific function of the orientation determination unit 18 will be described later with reference to FIG. 2.

Figure 2:
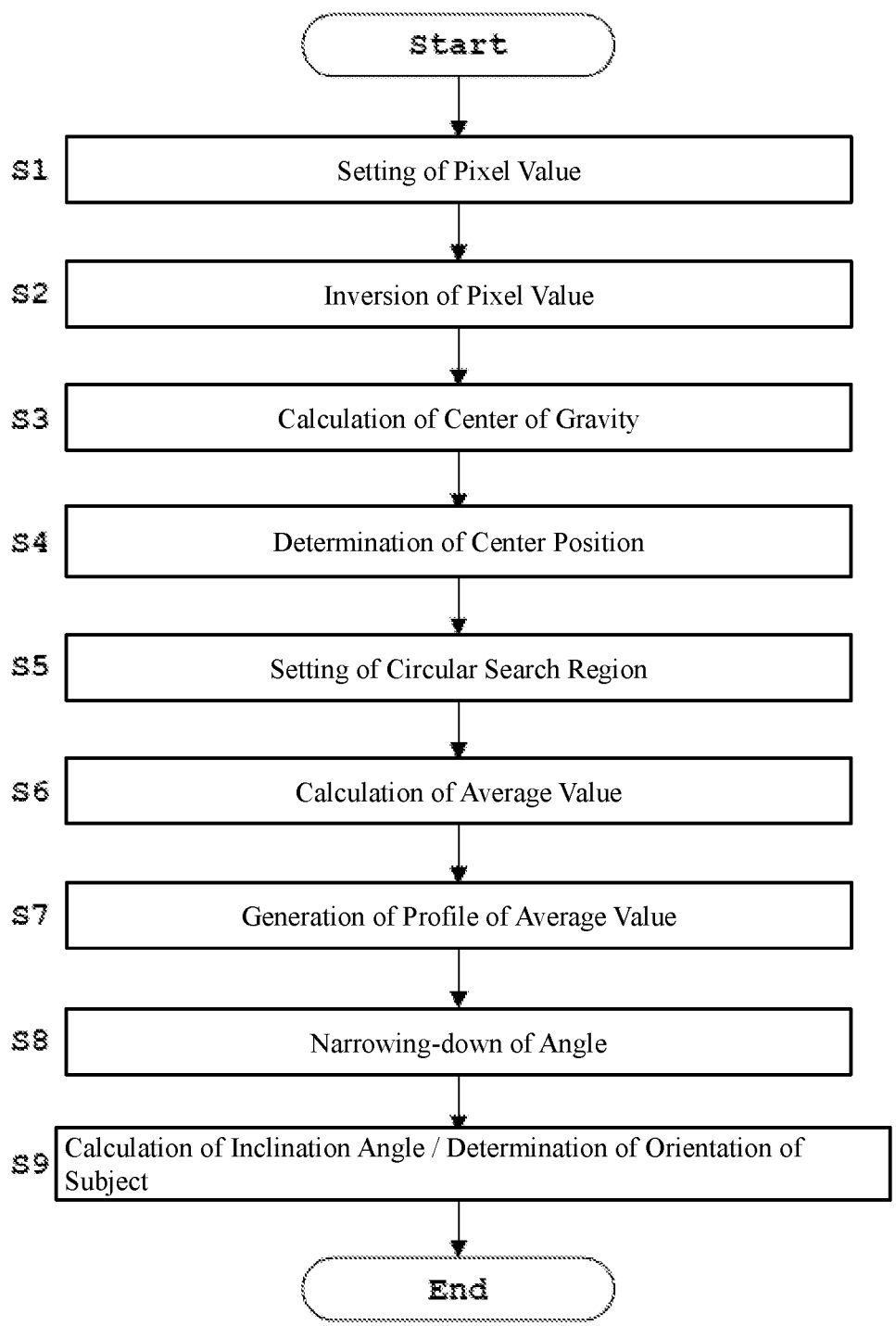
FIG. 2 is a flowchart of an image processing method according to an example.
Figure 3:
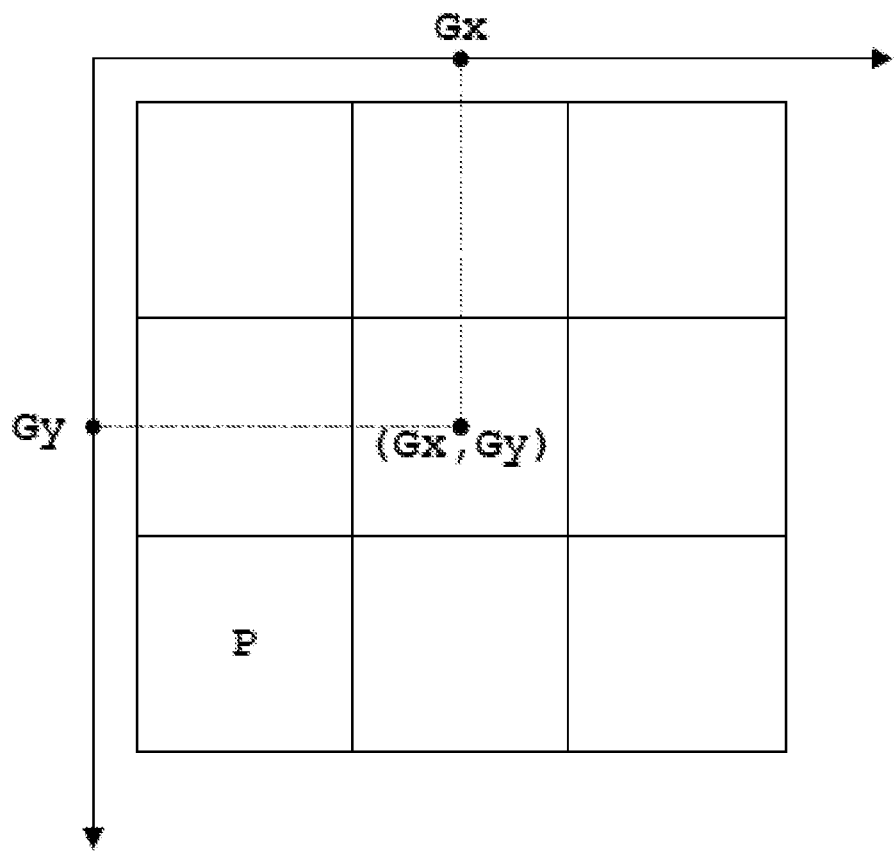
FIG. 3 is a schematic diagram used for explaining when a vicinity pixel position of the center of gravity is obtained.
Figure 4:
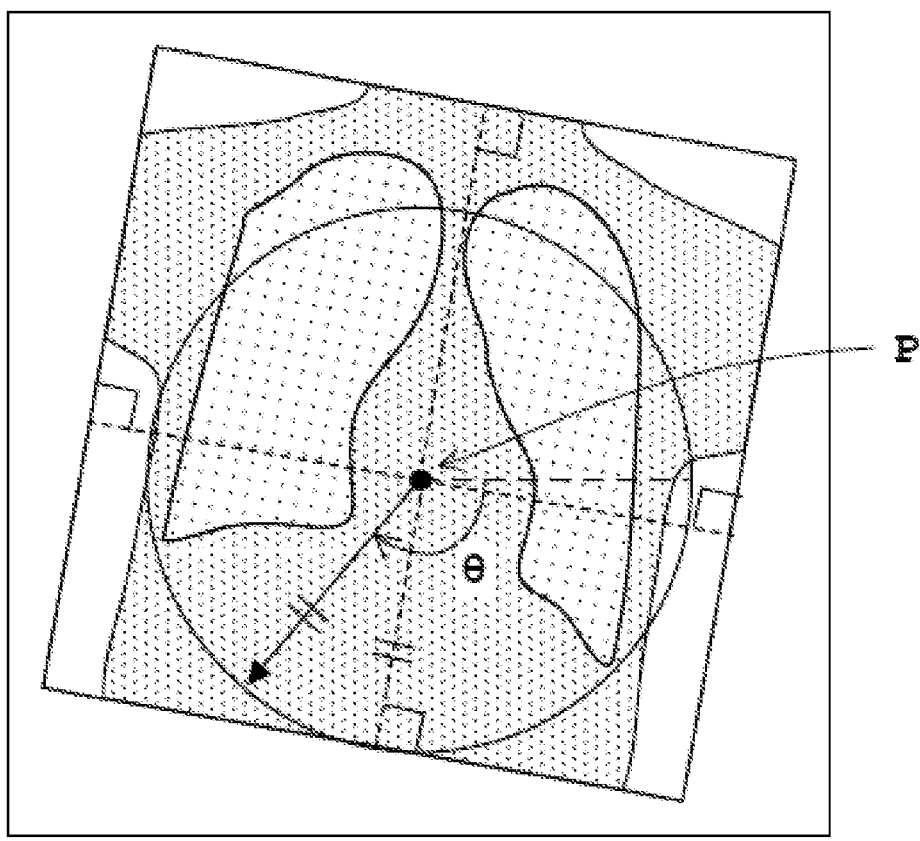
FIG. 4 is a schematic diagram of a chest front image used for explaining when a circular search region is set.
Figure 5:
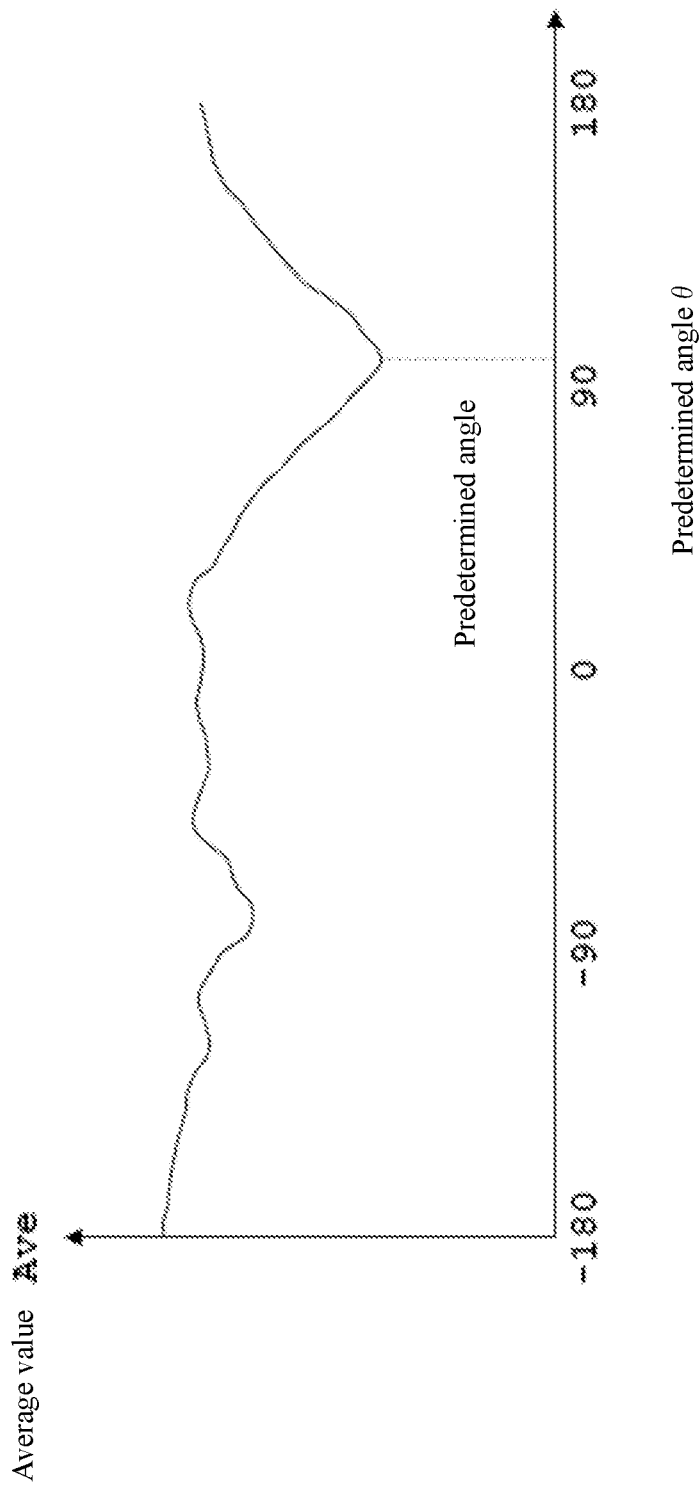
FIG. 5 is a schematic diagram of a profile of an average value in which a predetermined angle is shown on the horizontal axis and an average value is shown on the vertical axis.
Figure 6:
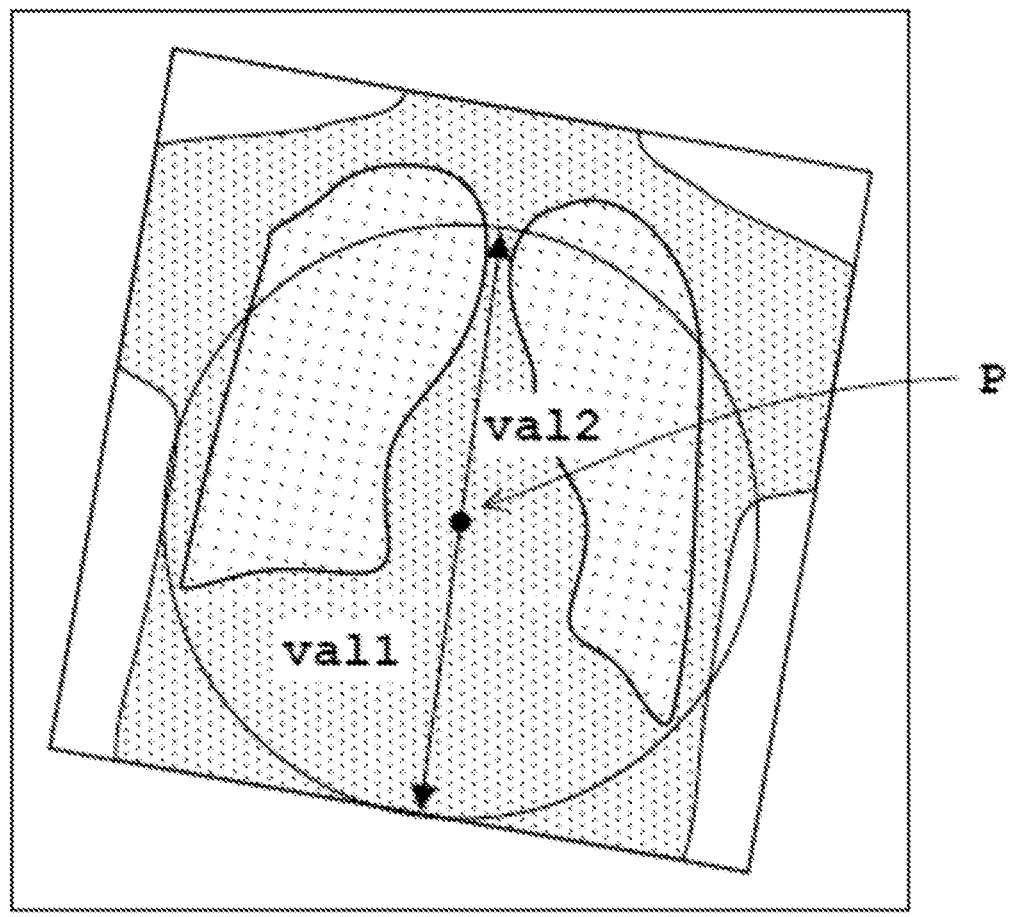
FIG. 6 is a schematic diagram of a chest front image used for explaining when an inclination angle is obtained.
Figure 7:
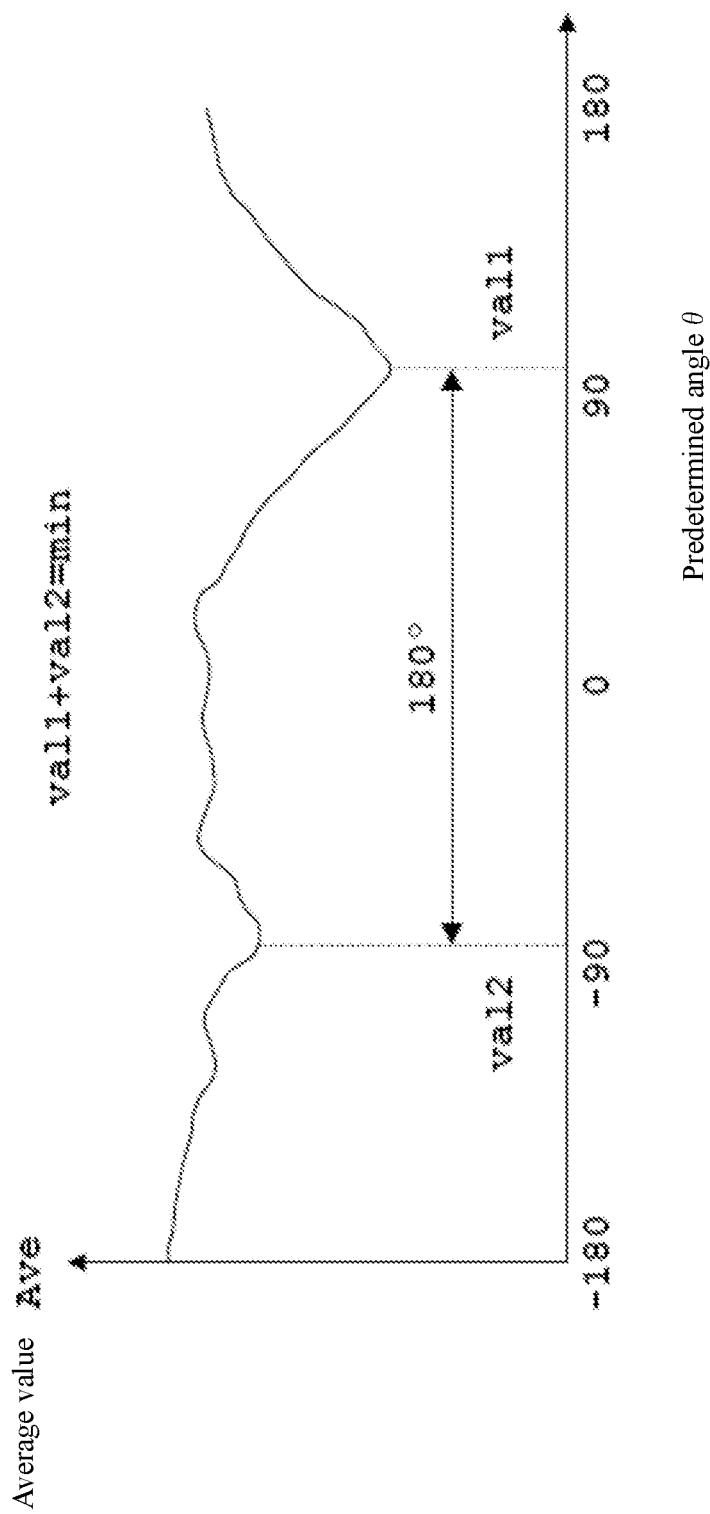
FIG. 7 is a schematic diagram of a profile of an average value used for explaining when an inclination angle is obtained.
Figure 8:
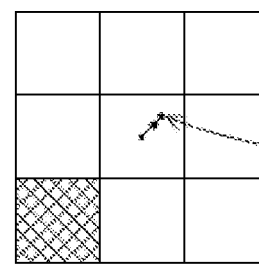
FIG. 8 is a schematic diagram used for explaining a reason for inverting pixel values.
Figure 9:
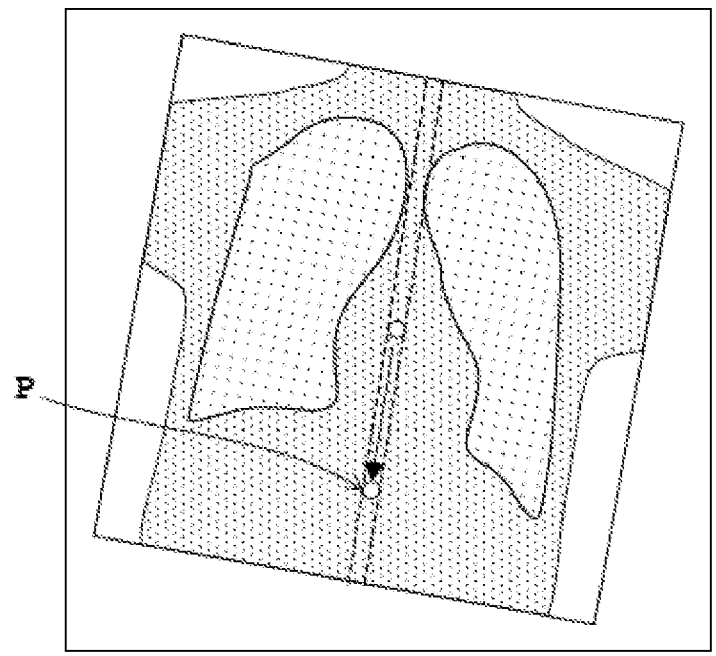
FIG. 9 is a schematic diagram used for explaining the reason that a pixel value in a chest front image is set by replacing the pixel value with the threshold value when the pixel value is lower than the threshold value.
Figure 9:
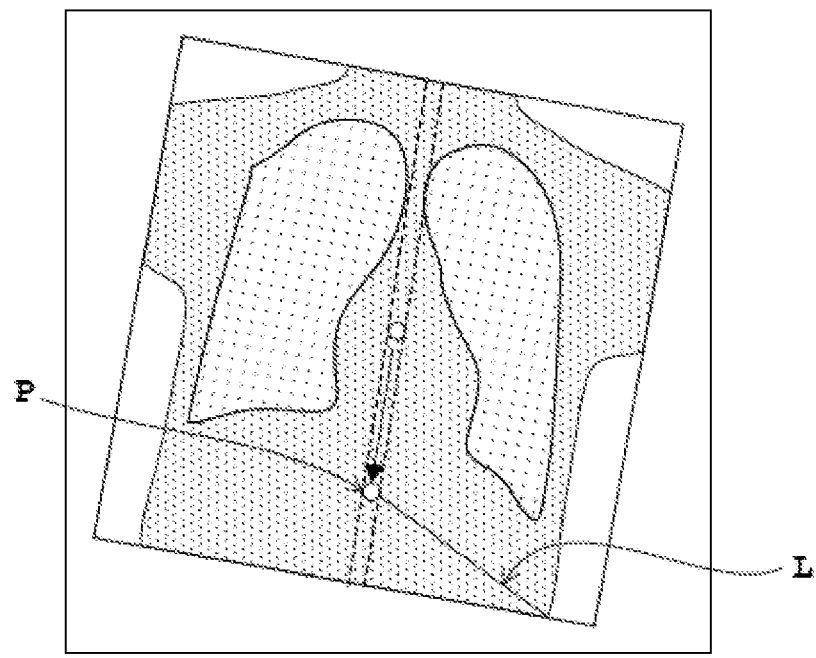

Next, the specific functions of the pixel value setting unit 11, the pixel value inversion unit 12, the center of gravity calculation unit 13, the vicinity pixel position calculation unit 14, the search region setting unit 15, the average value profile calculation unit 16, the inclination angle calculation unit 17, and the orientation determination unit 18 will be described with reference to FIG. 2 to FIG. 7. FIG. 2 is a flowchart of an image processing method according to an example. FIG. 3 is a schematic diagram used for an explanation when a vicinity pixel position of the center of gravity is obtained. FIG. 4 is a schematic diagram of a chest front image used for explaining when a circular search region is set. FIG. 5 is a schematic view showing a profile of an average value in which the predetermined angle is shown on the horizontal axis and the average value is shown on the vertical axis. FIG. 6 is a schematic diagram of a chest front image used for explaining when the inclination angle is obtained. FIG. 7 is a schematic diagram of a profile of an average value used for explaining when the inclination angle is obtained.

(Step 51) Setting of Pixel Value

When a coordinate of a pixel is x, y, a pixel value is I(x, y), and a preset threshold value is th, the pixel value setting unit 11 (see FIG. 1) sets the pixel value I(x, y) as shown in the following formula (1).

$$\{ \text{If } I(x, y) < th \Rightarrow I(x, y) = th \atop \text{else } I(x, y) = I(x, y) \} \quad (1)$$

As described in the above-described formula (1), when the pixel value I(x, y) in chest front image is smaller than the threshold value th (If I(x, y)<th), it is set such that the pixel value I(x, y) is replaced with the threshold value th (I(x, y)=th), and when the pixel value I(x, y) in the chest front image is equal to or higher than the threshold value th (else), it is set such that the pixel value I(x, y) is set as the value I(x, y) of the pixel value itself without replacing the pixel value I(x, y) (I(x, y)=I(x, y)). The reason why the pixel value I(x, y) is replaced with the threshold value th when the pixel value I(x, y) in the chest front image is smaller than the threshold value th is described in the section of the "Means for Solving the Problems", and therefore is omitted here. Note that Step S1 corresponds to the pixel value setting step in the present invention.

(Step S2) Inversion of Pixel Value

When a pixel value in which a gradation becomes maximum is Imax, the pixel value inversion unit 12 (see FIG. 1) inverts the pixel value I(x, y) in the chest front image set by the pixel value setting unit 11 as shown in the above-described formula (1) as shown in the equation (2) described below.

$$I_{max} - I(x, y) \quad (2)$$

For example, in cases where the pixel value Imax in which the gradation becomes maximum is 14 bits (that is, when the gradation value is assigned to 0 to 214-1:0 to 16383), when 16383 is assigned to the Imax in the above formula (2), the pixel value after the inversion is 16383-I (x, y). The reason why the pixel value I(x, y) is inverted is also described in the section "Means for Solving the Problems", and therefore is omitted here. In cases where a subject is an adult, the centrum is positioned near the center of the image, but the center of gravity can be obtained in Step S3 to be described later without being affected by whether the pixel value I(x, y) has been inverted. Therefore, the inversion of the pixel value I(x, y) in Step S2 is performed regardless of whether a subject is a child or an adult. Note that Step S2 corresponds to the pixel value inversion step in the present invention.

(Step S3) Calculation of Center of Gravity

When the center of gravity of the x-coordinate is Gx and the center of gravity of the y-coordinate is Gy, the center of gravity calculation unit 13 (see FIG. 1) obtains the center of gravity Gx, Gy of the chest front image as in the following formulas (3) and (4) by the center of gravity calculation using the pixel value (Imax-I(x, y)) inverted by the pixel value inversion unit 12 in the chest front image as shown in the above-described formula (2). Note that Step S3 corresponds to the center of gravity calculation step in the present invention.

$$Gx = \frac{\sum_y \sum_x x(I_{max} - I(x, y))}{\sum_y \sum_x (I_{max} - I(x, y))} \quad (3)$$

$$Gy = \frac{\sum_y \sum_x y(I_{max} - I(x, y))}{\sum_y \sum_x (I_{max} - I(x, y))} \quad (4)$$

(Step S4) Determination of Center Position

The vicinity pixel position calculation unit 14 (see FIG. 1) determines the vicinity pixel position of the center of gravity Gx, Gy as the center position P as shown in FIG. 3. Specifically, in the chest front image in which the pixel value I(x, y) is not inverted, like the above-described formula (3) and formula (4), the coordinate of the pixel in which the pixel value I(x, y) becomes minimum in the rectangular region centered on the center of gravity Gx, Gy obtained by the center of gravity calculation unit 13. The coordinate is determined as the vicinity pixel position of the center of gravity Gx, Gy. The vicinity pixel position is determined as the center position P (see FIG. 3). The range of the rectangular region may be set as appropriate according to the resolution of the image, the compression ratio of the image, and the like.

When the irradiation field is compressed into an image consisting of 90×90 pixels vertically and horizontally in a 17 inches×17 inches square, the length of 17 inches (=431.8 mm) corresponds to 90 pixels, so the one pixel has a length of 4.80 mm (=431.8/90 mm). In this case, for example, in FIG. 3, it is set such that a rectangular region consists of 3×3 pixels vertically and horizontally. Note that the rectangular region is not limited to a square and when the irradiation field is a rectangle, the rectangular region is also set to a rectangle.

(Step S5) Setting of Circular Search Region

The search region setting unit 15 (see FIG. 1) sets the vicinity pixel position of the center of gravity Gx, Gy as a center of a circular search region having a radius of a predetermined length. The radius of the circular search region is set to a shortest line segment of four line segments obtained by drawing perpendicular lines down from the center position P (see also FIG. 4) which is the vicinity pixel position to the boundary lines of the upper, lower, left, and right irradiation fields.

For example, in the case of FIG. 4, since the line segment obtained by drawing a perpendicular line down from the center position P to the boundary line of the lower irradiation field is shortest. Therefore, the line segment obtained by drawing a perpendicular line to the boundary line of the lower irradiation field is set to a radius, and the circular search region centered on the center position P is set. The reason why the shortest line segment of four line segments obtained by drawing perpendicular lines down from the center position P to the boundary lines of the upper, lower, left, and right irradiation fields is set to a radius of the circular search region radius is to prevent pixels outside the irradiation field from being included in the circular search region. Note that Step S5 corresponds to the search region setting step in the present invention.

(Step S6) Calculation of Average value

In a chest front image, the pixel value I(x, y) generally becomes smaller at the lower portion of the centrum. Therefore, the average value profile calculation unit 16 (see FIG. 1) obtains the average value of the pixel values I(x, y) on a line segment which is a radius of the circular search region. As shown in FIG. 4, the line segment is rotationally displaced for each predetermined angle to obtain an average value for each predetermined angle. In FIG. 4, it is defined such that a predetermined angle is θ in which the horizontal axis extending rightward from the center position P is 0° and an angle rotationally displaced clockwise is a positive angle. Note that the average value is denotes as Ave (see FIG. 5).

(Step S7) Generation of Profile of Average value

As shown in FIG. 5, a profile of an average value is generated with the predetermined angle shown on the horizontal axis and the average value shown on the vertical axis. Note that Step S6 and Step S7 correspond to the evaluation value profile calculation step in the present invention.

(Step S8) Narrowing of Angle

By obtaining the displacement angle θ of the line segment in which the average value Ave becomes a minimum value in the average value profile shown in FIG. 5, the narrowing of the angles of the subject reflected in the chest front image is performed.

(Step S9) Calculation of Inclination Angle/Determination of Orientation of Subject After performing the narrowing of angles of the subject, the inclination angle calculation unit 17 (see FIG. 1) obtains the displacement angle θ of two line segments (diameter line segment) in which the sum of the average values of two line segments (diameter line segment) opposed at 180° in the profile of the average value shown in FIG. 5 becomes a minimum value as shown in FIG. 7 as the inclination angle of the chest front image. In FIG. 7, the minimum value is denotes as "min", the average value on the line segment estimated to extend to the lower portion of the centrum is denoted as "val1" (see also FIG. 6), and the average value on the line segment that is 180° opposite to the line segment (that is, the line segment estimated to extend to the upper portion of the centrum) is denoted as "val2" (see also FIG. 6). The displacement angle θ of two line segments (diameter line segment) satisfying val1+val2=min is obtained as the inclination angle.

The reason why the displacement angle θ of two line segments (diameter line segment) satisfying val1+val2=min is obtained as a displacement angle θ in Step 9 without obtaining the angle that was narrowed down in Step S8 is as follows. That is, if the inclination angle is determined only by the displacement angle θ at which the average value Ave on a line segment which is a radius of the circular search region becomes a minimum value, there is a risk of being unable to determine accurately the orientation of the subject. Furthermore, there may be a case in which a line segment in which the evaluation value becomes a minimum value is not necessarily correspond to the lower portion of the centrum due to the pixel value I(x, y) in the lower abdomen lower than the pixel value I(x, y) in the centrum.

Therefore, the orientation determination unit 18 (see FIG. 1) determines the orientation of the subject reflected in the chest front image from the inclination angle obtained by the inclination angle calculation unit 17. The inclination angle obtained by the inclination angle calculation unit 17 is converted to an angle φ(−180°≤φ≤180°) which is an angle of the line segment extending to the upper portion of the centrum relative to the vertical angle 0° of the image with a counterclockwise rotation as a positive angle. In a chest front image in which a subject is an adult, the upper, lower, right, and left directions of the subject are determined according to the size of the angle φ as follows.

−45°≤φ≤45°→oriented upward

−180°≤φ≤−135°, or 135°≤φ≤180°→oriented downward

45°≤φ≤135°→oriented leftward

−135°≤φ≤−45°→oriented rightward

Note that "oriented upward" denotes that the head of the subject is positioned at the upper portion of the screen. "Oriented upward" denotes that the head of the subject is positioned at the lower portion of the screen. "Oriented leftward" denotes that the head of the subject is positioned on the left side of the screen. "Oriented rightward" denotes that the head of the subject is positioned on the right side of the screen. Note that Step S9 corresponds to an inclination angle calculation step and an orientation determination step in the present invention.

According to the image processing method of this example, in the center of gravity calculation step (Step S3), the center of gravity Gx, Gy of the chest front image is obtained by the center of gravity calculation using the pixel value I(x, y) in the chest front image. As described above, the pixel value I(x, y) in the centrum of a subject centrum is low. Therefore, it is estimated that the center of gravity Gx, Gy of the chest front image obtained by the center of gravity calculation using the pixel value I(x, y) in the chest front image or its vicinity pixel position is positioned on the centrum. In the search region setting step (Step S5), the center of gravity Gx, Gy or its vicinity pixel position is set as the center of the circular search region having a radius of a predetermined length (see center position P in FIG. 3, FIG. 4, and FIG. 6). In the evaluation value profile calculation step (Step S6 and Step S7), the average value Ave of the pixel value I(x, y) on the line segment which is a radius of the circular search region is set as an evaluation value, and a profile of an evaluation value (average value Ave) for each predetermined angle θ is obtained by rotationally displacing the line segment for every predetermined angle θ.

As described in the section of "Means for Solving the Problems", in the chest front image, since there are bronchus at the upper portion and internal organs at the lower portion, the pixel value I(x, y) becomes generally smaller at the lower portion of the centrum. Therefore, in the orientation determination step (determination of the orientation of the subject in Step S9), the line segment in which the evaluation value (average value Ave) becomes a minimum value is estimated to correspond to the lower portion of the centrum, and the orientation of the subject reflected in the chest front image and oriented from the head to the abdomen can be determined from the displacement angle θ of the line segment in which the evaluation value (average value Ave) becomes a minimum value.

On the other hand, in the inclination angle calculation step (calculation of the inclination angle in Step S9), the displacement angle θ of two line segments (diameter line segment) in which the sum (val1+val2) of evaluation values (average values Ave) on two line segments (diameter line segment) opposed at 180° in the profile of the evaluation value (average value Ave) becomes a minimum value is obtained as the inclination angle of the chest front image. The two line segments (diameter line segment) in which the sum (val1+val2) of evaluation values (average values Ave) becomes a minimum value are estimated to correspond to the entire centrum including the upper portion of the centrum, and the inclination angle of the chest front image can be obtained with higher accuracy. As a result, the orientation of the subject reflected in the chest front image can be detected with high accuracy.

In this example, the vicinity pixel position of the center of gravity Gx, Gy is a coordinate of the pixel where the pixel value I(x, y) becomes minimum in the rectangular region centered on the center of gravity Gx, Gy. In cases where the center of gravity Gx, Gy of the chest front image obtained by the center of gravity calculation using the pixel value I(x, y) in the chest front image is not positioned on the centrum, the coordinate of the pixel is finely adjusted so that the vicinity pixel position of the center of gravity is positioned on the centrum by searching the coordinate of the pixel in which the pixel value I(x, y) becomes minimum in the rectangular region centered on the center of gravity Gx, Gy as shown in FIG. 3 and setting the coordinate as the center (center position P) of the circular search region (Step S4). As described above, the range of the rectangular region may be set as appropriate according to the resolution of the image, the compression ratio of the image, and the like.

As described in the section of "Means for Solving the Problems", in cases where a subject is a child, the centrum may sometimes deviate significantly from the center of the image. In that case, significant misalignment occurs between the center of gravity and the centrum in the chest front image obtained by the center of gravity calculation using the pixel value I(x, y) in the chest front image. Therefore, even if a method is adopted in which the coordinate of the pixel in which the pixel value I(x, y) becomes minimum in the rectangular region centered on the center of gravity Gx, Gy is set as the vicinity pixel position of the center of gravity Gx, Gy, the rectangular region which becomes a search range becomes very large, so that the amount of calculation increases. Alternatively, even if the rectangular region which becomes a search range is expanded, the pixel in which the pixel value I(x, y) in the rectangular region becomes minimum is not necessarily positioned on the centrum. Therefore, in this example, preferably, a pixel value inversion step (Step S2) of inverting the pixel value I(x, y) in the chest front image is provided, and in the above-described center of gravity calculation step (Step S2), the center of gravity Gx, Gy is calculated by the center of gravity calculation using the inverted pixel value (Imax-I(x, y)).

Further, in this example, both the above-mentioned method in which the coordinate of the pixel in which the pixel value I(x, y) becomes minimum in the rectangular region centered on the center of gravity Gx, Gy is set to the vicinity pixel position of the center of gravity Gx, Gy and the above-mentioned method in which the center of gravity Gx, Gy is obtained by the center of gravity calculation using the inverted pixel value (Imax-I(x, y)) are combined.

That is, in the case of this example, the pixel value inversion step (Step S2) of inverting a pixel value I(x, y) in the chest front image is provided, in the above-described center of gravity calculation step (Step S2), the center of gravity Gx, Gy is obtained by the center of gravity calculation using the inverted pixel value (Imax-I(x, y)), and the vicinity pixel position of the center of gravity Gx, Gy is the coordinate of the pixel in which the pixel value I(x, y) becomes minimum in the rectangular region centered on the center of gravity Gx, Gy in the chest front image where the pixel value I(x, y) is not inverted. In other words, when the center of gravity Gx, Gy is obtained, the inverted pixel value (Imax-I(x, y)) is used, and when the coordinate of the pixel in which the pixel value I(x, y) becomes minimum in the rectangular region centered on the center of gravity Gx, Gy is set as the vicinity pixel position of the center of gravity Gx, Gy, a chest front image in which the pixel value I(x, y) is not inverted is used.

As described above, the pixel value I(x, y) is small in the lower abdomen as well as the centrum. Therefore, when a method of calculating the center of gravity Gx, Gy by the center of gravity calculation using the inverted pixel value (Imax-I(x, y)) like this example is adopted, there is a possibility that the center of gravity Gx, Gy or its vicinity pixel position is positioned in the lower abdomen of the centrum where there exist no lung fields. Therefore, in this example, preferably, the pixel value setting step (Step S1) is provided in which when a pixel value I(x, y) in the chest front image is lower than a preset threshold value, the pixel value I(x, y) is set by replacing the pixel value I(x, y) with the threshold value th, and when the pixel value I(x, y) in the chest front image is equal to or higher than the threshold value th, the pixel value is set as the value I(x, y) itself without replacing the pixel value with the threshold value, in the pixel value inversion step (Step S2) described above, the pixel value I(x, y) set in the pixel value setting step (Step S1) is inverted, and in the center of gravity calculation step (Step S3) described above, the center of gravity Gx, Gy of the chest front image is obtained by the center of gravity calculation using the inverted pixel value (Imax-I (x, y)).

In this example, in the search region setting step (Step S5), the shortest line segment of the four line segments obtained by drawing perpendicular lines down from the center of gravity Gx, Gy or its vicinity pixel position to the boundary lines of the irradiation field is set as a radius of the circular search region. By setting the shortest line segment of the four line segments obtained by drawing perpendicular lines from the center of gravity Gx, Gy or its vicinity pixel position to the boundary lines of the irradiation field as a radius of the circular search region, the pixels outside the irradiation field are prevented from being included in the circular search region.

In this example, the orientation of the subject is determined in the orientation determination step (determination of the orientation of the subject in Step S9) from the inclination angle obtained in the inclination angle calculation step (calculation of the inclination angle in Step S9). As described in the section "Means for Solving the Problems", only with the displacement angle θ at which the evaluation value (average value Ave) is a minimum value, the orientation of the subject may not be determined accurately when there is a plurality of inclination angles θ at which the evaluation value (average value Ave) becomes a minimum value. Furthermore, there may be a case in which a line segment in which the evaluation value (average value Ave) becomes a minimum value does not necessarily correspond to the lower portion of the centrum due to the pixel value I(x, y) in the lower abdomen higher than the pixel value I(x, y) in the centrum.

Therefore, in the inclination angle calculation step (calculation of the inclination angle in Step S9), the displacement angle θ of two line segments (diameter line segment) in which the sum (val1+val2) of evaluation values (average values Ave) on two line segments (diameter line segment) opposed at 180° in the profile of the evaluation value (average value Ave) becomes a minimum value is obtained as the inclination angle of the chest front image. With this, it is possible to narrow down the inclination angle of two line segments (diameter line segment) in which the sum (val1+val2) of evaluation values becomes a minimum value from candidates for the displacement angle θ in which the evaluation value (average value Ave) on a plurality of narrowed-down line segments as an inclination angle of the chest front image. Further, even if the line segment in which the evaluation value (average value Ave) becomes a minimum value does not necessarily correspond to the lower portion of the centrum due to the pixel value I(x, y) in the lower abdomen lower than the pixel value I(x, y) in the centrum, it is possible to obtain the displacement angle of the two line segments (diameter line segment) as the inclination angle of the chest front image in consideration of the evaluation value (average value Ave) of the line segment opposed at 180° corresponding to the upper portion of the centrum. Then, in the above-described orientation determination step (orientation of the subject in Step S9), the orientation of the subject can be accurately determined from the obtained inclination angle. Therefore, by obtaining the inclination angle strictly in the inclination angle calculation step (calculation of the inclination angle in Step S9) and thereafter determining the orientation of the subject in the orientation determination step (determination of the orientation of the subject in Step S9), the orientation of the subject can be determined accurately.

It should be noted that the present invention is not limited to the aforementioned embodiments, and can be modified as follows.

(1) In the above-described example, although the description is made by exemplifying an image obtained by performing X-ray imaging by a mobile vehicle (mobile X-ray imaging apparatus) as a chest front image, an image is not necessarily required to be an image obtained by performing X-ray imaging by a mobile vehicle. For example, an image may be an image obtained by performing X-ray imaging with a C-arm.

(2) In the above-described example, although the description is made by exemplifying an average value as an evaluation value, but the evaluation value may be an addition value.

(3) In the above-described example, as shown in FIG. 3, although the vicinity pixel position of the center of gravity Gx, Gy is a coordinate of the pixel in which the pixel value I(x, y) becomes minimum in the rectangular region centered on the center of gravity Gx, Gy and the position of the center of gravity is determined as a center position P of the circular search region, the center of position P is not limited to the vicinity pixel position. When the center of gravity Gx, Gy is positioned on the centrum, the center of gravity Gx, Gy may be determined as the center position P of the circular search region.

(4) In the above-described example, although the pixel value inversion step (Step S2) of inverting a pixel value I(x, y) in the chest front image is provided, in cases where the a subject is an adult or the centrum is positioned near the center of the image, it is not always necessary to invert the pixel value I(x, y). Further, even in cases where a subject is a child and the centrum may deviate significantly from the center of the image, as described in the section of "Means for Solving the Problems", what is to obtain ultimately is not the position of the center of gravity but the orientation and/or the inclination angle of the subject. Therefore, in cases where the pixel value I(x, y) is not inverted when the centrum deviates significantly from the center of the image, the background region outside the subject is merely included in the circular search region with the line segment as a radius, so the orientation and/or the inclination angle of the subject can be determined with a certain degree of accuracy. However, in order to obtain the orientation and/or the inclination angle of the subject more accurately, preferably, the pixel value I(x, y) is inverted as in the above-described example, and the center of gravity Gx, Gy is obtained by the center of gravity calculation using the inverted pixel value (Imax-I (x, y)).

(5) In the above-described example, both the method in which the coordinate of the pixel in which the pixel value I(x, y) becomes minimum in the rectangular region centered on the center of gravity Gx, Gy is set as the vicinity pixel position of the center of gravity Gx, Gy and the method in which the center of gravity Gx, Gy is obtained by the center of gravity calculation using the inverted pixel value (Imax-I(x, y)) are combined. However, it is not always necessary to combine both of two methods described above. For example, when the center of gravity Gx, Gy obtained by the center of gravity calculation using the inverted pixel value (Imax-I (x, y)) is positioned on the centrum, the center of gravity Gx, Gy may be determined as the center position P of the circular search region.

(6) In the above-described example, when the method of calculating the center of gravity Gx, Gy by the center of gravity calculation using the inverted pixel value (Imax-I (x, y)) is adopted, in Step S1, the pixel value I(x, y) in the lower abdomen is rounded to the threshold value th. However, it is not always necessary to round the pixel value I(x, y) in the lower abdomen to the threshold value th. For example, when image processing is performed using a chest front image in which the irradiation field is reflected only in the lung field region and there is no lower abdomen, the lower abdomen is not reflected in the chest front image. Therefore, even in cases where the method of calculating the center of gravity Gx, Gy by the center of gravity calculation using the inverted pixel value (Imax-I (x, y)), it is not always necessary to round the pixel value I(x, y) to the threshold value th.

(7) In the above-described example, in cases where a method in which the center of gravity Gx, Gy is obtained by the center of gravity calculation using the inverted pixel value (Imax-I(x, y)) is adopted, in Step S1, the pixel value I(x, y) in the lower abdomen is rounded to the threshold value th, and further the coordinate of the pixel in which the pixel value I(x, y) becomes minimum in the rectangular region centered on the center of gravity Gx, Gy is set as the vicinity pixel position of the center of gravity Gx, Gy. However, it is not necessary to combine all of these methods. For example, when the method of calculating the center of gravity Gx, Gy by the center of gravity calculation using the inverted pixel value (Imax-I (x, y)) is adopted, in Step S1, the pixel value I(x, y) in the lower abdomen may be rounded to the threshold value th, and when the center of gravity Gx, Gy obtained by the center of gravity calculation using the inverted pixel value (Imax-I (x, y)) rounded to the threshold value th is positioned on the centrum, the center of gravity Gx, Gy may be determined as the center position P of the circular search region.

(8) In the above-described example, although the shortest line segment of the four line segments obtained by drawing perpendicular lines down from the center of gravity Gx, Gy or its vicinity pixel position to the boundary lines of the radiation field is set as the radius of the circular search region, the shortest line segment is not necessarily set as a radius of the circular search region. For example, a line segment having a predetermined length shorter than the shortest line segment may be set as a radius of the circular search region. However, according to the method of setting the shortest line segment as a radius of the circular search region as in the above-described example, more pixel information is included in the circular search region. Therefore, it is preferable to set the shortest line segment like the example as a radius of the circular search region. Therefore, in the method of the example, the orientation of the subject can be determined with higher accuracy, and the inclination angle of the chest front image can be determined with higher accuracy.

(9) In the above-described example, although the orientation of the subject is determined in the above-described orientation determination step (orientation of the subject in Step S9) from the inclination angle obtained in the above-described inclination angle calculation step (calculation of the inclination angle in Step S9), the order of the above-described orientation determination step (determination of the orientation of the subject in Step S9) and the above-described inclination angle calculation step (calculation of the inclination angle in Step S9) is not particularly limited. For example, in cases where the displacement angle θ at which the evaluation value (average value Ave in the above example) becomes a minimum value is only one and the lower abdomen is not reflected in the chest front image, the orientation of the subject may be determined from the displacement angle θ at which the evaluation value (average value Ave) becomes a minimum value. Therefore, the inclination angle calculation step (calculation of the inclination angle in Step S9) may be performed after the orientation determination step (determination of the orientation of the subject in Step S9).

(10) In the above-described example, in the profile of the evaluation value (profile of the average value Ave shown in FIG. 5 in the above example), the displacement angle θ of the line segment in which the evaluation value (average value Ave) becomes a minimum value is obtained, and then the displacement angle θ of the two lines segments (diameter line segment) in which the sum (val1+val2) of the evaluation values (average value Ave) on the two line segments (diameter line segment) opposed at 180° in the profile of the evaluation value (profile of the average value Ave shown in FIG. 7) becomes a minimum value is obtained, but the order of obtaining each displacement angle θ which becomes a minimum value is not particularly limited. For example, in cases where the displacement angle θ in which the evaluation value (average value Ave) as described above becomes a minimum value is only one and the lower abdomen is not reflected in the chest front image, first, the displacement angle θ of two line segments (diameter line segment) in which the sum (val1+val2) of the evaluation values (average value Ave) on the two line segments (diameter line segment) opposed at 180° becomes a minimum value is obtained, and then the smaller values in the magnitude relationship between val1 and val2 is obtained as a minimum value, and the displacement angle θ at that time is obtained.

INDUSTRIAL APPLICABILITY

As described above, the present invention is suitable for image processing of a chest front image obtained by performing X-ray imaging by a mobile vehicle (mobile X-ray imaging apparatus).

DESCRIPTION OF REFERENCE SYMBOLS

1: image processing apparatus
x, y: coordinate of a pixel
I(x, y): pixel value
Th: threshold value
Imax: pixel value in which gradation becomes maximum
Imax-I(x, y): inverted pixel value
Gx, Gy: center of gravity
P: center position
θ: predetermined angle, displacement angle
Ave: average value
val1: average value on a line segment extending toward the lower portion of the centrum
val2: average value on a line segment extending toward the upper portion of the centrum

The invention claimed is:
1. An image processing method of a chest front image, comprising:

a center of gravity calculation step of obtaining a center of gravity of a chest front image by a center of gravity calculation using pixel values in the chest front image;

a search region setting step of setting the center of gravity or its vicinity pixel position as a center of a circular search region having a radius of a predetermined length;

an evaluation value profile calculation step of obtaining a profile of an evaluation value for each predetermined angle by setting an average value or an addition value of pixel values on a line segment which is a radius of the circular search region or two line segments including the line segment and a line segment opposed to the line segment at 180° as the evaluation value; and an inclination angle calculation step of obtaining a displacement angle of the line segment in which the evaluation value becomes a minimum value in the profile of the evaluation value or the two lines segments as an inclination angle of the chest front image.

2. The image processing method as recited in claim 1, wherein the vicinity pixel position is a coordinate of a pixel in which a pixel value becomes minimum in a rectangular region centered on the center of gravity.

3. The image processing method as recited in claim 2, further comprising:

a pixel value inversion step of inverting pixel values in the chest front image, wherein in the center of gravity calculation step, the center of gravity is obtained by the center of gravity calculation using the inverted pixel values, and wherein the vicinity pixel position is the coordinate of the pixel in which the pixel value becomes minimum in the rectangular region centered on the center of gravity in the chest front image in which pixel values are not inversed.

4. The image processing method as recited in claim 1, further comprising:

a pixel value inversion step of inverting pixel values in the chest front image, wherein in the center of gravity calculation step, the center of gravity is obtained by the center of gravity calculation using the inverted pixel values.

5. The image processing method as recited in claim 4, further comprising:

a pixel value setting step of preforming setting of replacing a pixel value in the chest front image with a preset threshold value when the pixel value is lower than the preset threshold value, and performing setting the pixel value in the chest front image as a value of the pixel value itself without replacing the pixel value when the pixel value is equal to or higher than the threshold value, wherein in the pixel value inversion step, the pixel value set in the pixel value setting step is inverted, and wherein in the center of gravity calculation step, the center of gravity of the chest front image is obtained by the center of gravity calculation using the inverted pixel values.

6. The image processing method according to claim 1, wherein in the search region setting step, a shortest line segment of four line segments obtained by drawing perpendicular lines down from the center of gravity or its vicinity pixel position to boundary lines of an irradiation field is set as a radius of the circular search region.

7. The image processing method as recited in claim 1, wherein in the orientation determination step, the orientation of the subject is determined from the inclination angle obtained in the inclination angle calculation step.

* * * * *